US00PP29900P3

(12) United States Plant Patent
Bourne

(10) Patent No.: US PP29,900 P3
(45) Date of Patent: Nov. 27, 2018

(54) ***DIANTHUS* PLANT NAMED 'WP15 PIE45'**

(50) Latin Name: ***Dianthus* x *allwoodii* hort.**
Varietal Denomination: WP15 PIE45

(71) Applicant: Plant Genetics International Ltd., Hambrook, West Sussex (GB)

(72) Inventor: Carolyn Grace Bourne, Devon (GB)

(73) Assignee: Plant Genetics International Ltd., Hambrook (GB)

( * ) Notice: Subject to any disclaimer, the term of this patent is extended or adjusted under 35 U.S.C. 154(b) by 0 days.

(21) Appl. No.: 15/731,061

(22) Filed: Apr. 12, 2017

(65) Prior Publication Data

US 2017/0303455 P1 Oct. 19, 2017

(30) Foreign Application Priority Data

Apr. 15, 2016 (QZ) ..... PBR 2016/0942

(51) Int. Cl.
*A01H 5/02* (2018.01)
*A01H 6/30* (2018.01)

(52) U.S. Cl.
USPC ..... Plt./273
CPC ..... *A01H 5/02* (2013.01); *A01H 6/305* (2018.05)

(58) Field of Classification Search
USPC ..... Plt./272, 276, 281
CPC ..... A01H 5/0233; A01H 5/02; A01H 5/0227; A01H 6/305
See application file for complete search history.

(56) References Cited

PUBLICATIONS

Missouri Botanical Garden *Dianthus* (*Allwoodii* Alpinus Group), retrieved on Apr. 9, 2018, retrieved from the Internet at http://www.missouribotanicalgarden.org/PlantFinder/PlantFinderDetails.aspx?taxonid=259721&isprofile=0&, 2 pp. (Year: 2018).*

* cited by examiner

*Primary Examiner* — June Hwu
(74) *Attorney, Agent, or Firm* — Bethany R. Roahrig; Barbara Campbell; Cochran Freund & Young LLC

(57) ABSTRACT

A new cultivar of *Dianthus* plant named 'WP15 PIE45' that is characterized by large single flowers with an apricot-khaki colored eye delimited by a bright red-orange line, deep fimbriated petal edges, medium sweet fragrance, blooming from May through October, a compact mounding habit, glaucous blue green foliage and that is suitable for use as a flowering plant in pots and containers as well as for use as a cut flower and in bouquets, is disclosed.

2 Drawing Sheets

Genus and species: *Dianthus* x *allwoodii* hort.
Variety denomination: 'WP15 PIE45'.

CROSS REFERENCE TO RELATED APPLICATIONS

This application claims the benefit of priority under 35 U.S.C. 119 (f) to the application for European Community Plant Variety Rights which was filed for the instant plant variety on Apr. 15, 2016, File Number 2016/0942.

BACKGROUND OF THE NEW PLANT

The present invention relates to a new and distinct cultivar of hardy *Dianthus*, commonly known as Garden Pink, which is grown for use as a flowering plant for pots and containers and for planting in the garden and landscape. The new cultivar is known botanically as *Dianthus* x *allwoodii* hort. and will be referred to hereinafter by the cultivar name 'WP15 PIE45'.

'WP15 PIE45' was selected from the open pollination of a group of unnamed and unreleased seedlings of *Dianthus* in the group *Dianthus* x *allwoodii* hort. which is characterized by large single flowers. 'WP15 PIE45' is the product of a long-term breeding program conducted in a cultivated area of Houndspool, Dawlish, Devon, United Kingdom. 'WP15

PIE45' was selected in 2012 for its large single flowers with an apricot-khaki colored eye delimited by a bright red-orange line, deep fimbriated petal edges, medium sweet fragrance and glaucous blue-green foliage.

Asexual reproduction of 'WP15 PIE45' was first accomplished in 2012 in a cultivated area of Houndspool, United Kingdom using the propagation method of shoot cuttings. 'WP15 PIE45' has been determined to be stable and reproduces true to type in successive generations of asexual propagation.

SUMMARY

The following traits have been repeatedly observed and represent the characteristics of the new *Dianthus* cultivar 'WP15 PIE45'. 'WP15 PIE45' has not been tested under all possible conditions and phenotypic differences may be observed with variations in environmental, climatic and cultural conditions, however, without any variance in genotype.

1. 'WP15 PIE45' exhibits a compact mounding habit.
2. 'WP15 PIE45' bears single light pink-peach flowers with an apricot-khaki eye.
3. The petals of 'WP15 PIE45' are flat.
4. 'WP15 PIE45' blooms from May through October.

5. The flowers of 'WP15 PIE45' exhibit a medium sweet fragrance.
6. 'WP15 PIE45' exhibits glaucous blue green foliage.
7. At maturity, the height of the foliage mound of 'WP15 PIE45' is 40 cm, and the width is 30 cm to 35 cm.
8. 'WP15 PIE45' is perennial and is hardy at least to minus 15° Centigrade.
9. 'WP15 PIE45' is suitable for use as a flowering plant in pots and containers, and for use as a cut flower and in bouquets.

BRIEF DESCRIPTION OF THE PHOTOGRAPHS

The accompanying color photographs illustrate the overall appearance of the new *Dianthus* variety 'WP15 PIE45' showing colors as true as it is reasonably possible to obtain in colored reproductions of this type. Colors in the photographs may differ from the color values cited in the detailed botanical description, which accurately describe the actual colors of the new variety 'WP15 PIE45'.

Figure 1:
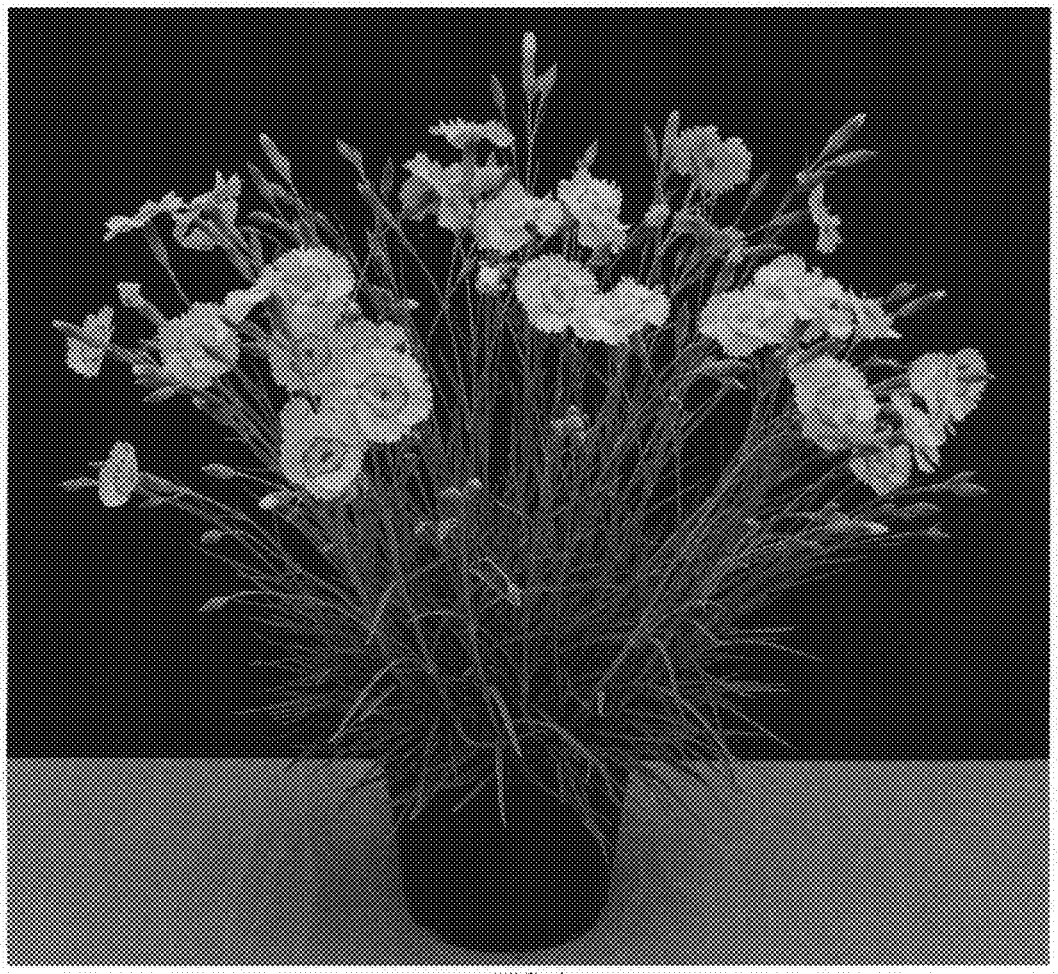
FIG. 1 depicts an entire flowering plant of 'WP15 PIE45'.
Figure 2:
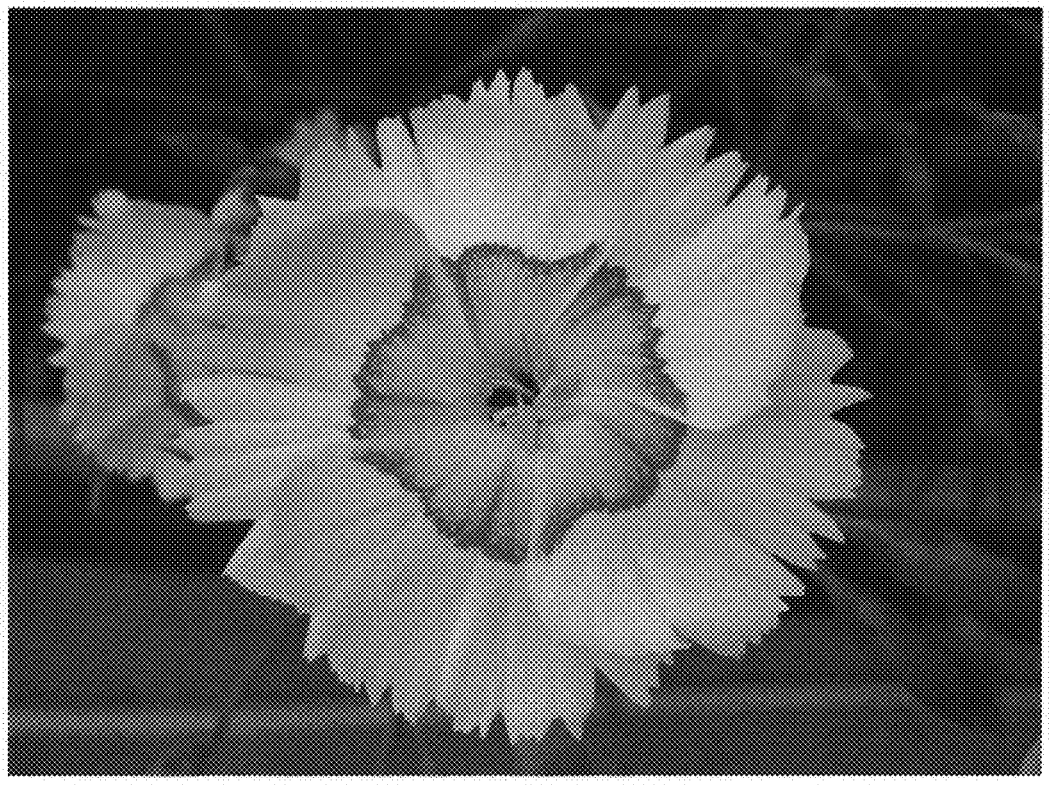
FIG. 2 depicts a close-up view of the flower of 'WP15 PIE45'.

Photographs were taken from a 9 months old plant which was growing in a glasshouse in a 3-liter container at the Inventor's nursery in Dawlish, Devon, United Kingdom. No chemicals were used to treat the plants. All photographs were made using conventional techniques and although colors may appear different from actual colors due to light reflectance they are as accurate as possible by conventional photography.

BOTANICAL DESCRIPTION OF THE PLANT

The following is a detailed description of the new cultivar 'WP15 PIE45'. Data was collected from plants grown in 3-liter containers under an unheated glasshouse in Houndspool, Dawlish, United Kingdom. The color determinations are in accordance with the sixth edition (2015) of The Royal Horticultural Society Colour Chart of The Royal Horticultural Society, London, England, except where general color terms of ordinary dictionary significance are used. No chemicals were used to treat the plants. Growing conditions are typical to other *Dianthus*.

Botanical classification: *Dianthus*.

*Variety*.—'WP15 PIE45'.

*Species*.—x *allwoodii* hort.

*Common names*.—Hybrid *dianthus*, Garden Pink.

*Commercial classification*.—Hardy perennial.

*Use*.—Ornamental plant for pots and containers.

Parentage: 'WP15 PIE45' resulted and was selected from the open pollination of a group of unnamed and unreleased seedlings of *Dianthus* in the group *Dianthus* x *allwoodii* hort.

Plant description:

*Bloom period*.—May to October.

*Plant habit*.—Compact mounding habit.

*Plant height*.—40 cm in overall height, including flower canopy.

*Plant width*.—30 cm to 35 cm in width.

*Plant hardiness*.—Hardy to minus 15° Centigrade.

*Type*.—Perennial.

*Root system*.—Fibrous.

*Propagation*.—Propagation is accomplished using shoot cuttings.

*Cultural requirements*.—Plant in full sun, well-drained and moderately fertile soil and keep well fertilized and watered.

*Time required to produce a rooted cutting*.—5 weeks are needed to produce a rooted cutting.

*Temperature recommended for cuttings to produce roots*.—The air temperature needed is a minimum of 15° Centigrade air temperature and base heat of 21° Centigrade.

*Crop time*.—6 to 9 months is needed to produce a finished 3-litre container size from a well-rooted cutting.

Stem:

*Shape*.—Cylindrical, solid.

*Dimensions*.—10 cm in length, 4 mm diameter.

*Surface*.—Glabrous and glaucous.

*Color*.—145B and 145C.

*Branching*.—Numerous shoots from the axils of the lower leaves.

*Internode length*.—4 mm to 6 mm between nodes (before extension of peduncle).

*Node dimensions*.—4 mm in diameter and 5 mm in length.

Leaf:

*Type*.—Evergreen.

*Dimensions*.—9 cm in length, 3 mm in width.

*Color* (*adaxial and abaxial surfaces*).—N189B and N189C.

*Shape*.—Linear.

*Division*.—Simple.

*Apex*.—Acute.

*Base*.—Decurrent.

*Venation*.—Absent on the adaxial surface and only one central vein visible on the abaxial surface.

*Margins*.—Entire.

*Attachment*.—Sheathing.

*Arrangement*.—Opposite and spiraling up stem.

*Curvature*.—Weakly recurved.

*Surfaces* (*adaxial and abaxial*).—Strongly glaucous.

*Fragrance*.—Absent.

Flowers:

*Inflorescence*.—Simple cyme.

*Type*.—Single, polypetalous.

*Number*.—5 to 9 per stem.

*Dimensions* (*including calyx*).—35 mm in length and 55 mm in diameter.

*Shape*.—Circular.

*Position*.—Flowers are borne far above the foliage.

*Internodes*.—On average (5 flowering stems), each stem presents 6 internodes between the lowest flower-bearing node and the epicalyx.

*Lastingness*.—10 days at 20° Celsius on the plant; 8 to 10 days off the plant.

*Fragrance*.—Medium, sweet.

*Flowering period*.—May to October.

Peduncle:

*Shape*.—Cylindrical, solid.

*Dimensions*.—25 cm to 30 cm in length, 2 mm in diameter.

*Surface*.—Glabrous, waxy.

*Strength*.—Strong, rigid.

*Color*.—N189B to N189C.

Bud:
*Shape*.—Cylindrical.
*Color*.—N138A to N138B on apical half and 144B to 144C on basal half (below the bracts).
*Anthocyanin*.—Absent.
*Dimensions*.—28 mm in length and 8 mm in width.

Petals:
*Corolla*.—Upper and lower part of corolla is flat.
*Petal arrangement*.—Persistent, apopetalous and overlapping.
*Margin*.—Irregularly serrate.
*Indentations*.—Up to 8 mm deep.
*Texture*.—Soft.
*Type*.—Single.
*Number of petals*.—5.
*Dimensions*.—56 mm in length, 35 mm in width.
*Petal shape*.—Fan shape.
*Petal undulation* (*side view*).—Moderate to strong undulation.
*Petal surfaces*.—Glabrous, abaxial surface irregularly papillate.
*Petal apex*.—Fan shaped, irregularly serrate margin, moderate number of indents.
*Petal base*.—Strap shaped, tapering towards base.
*Color pattern*.—Flower is opening into a light pink-peach base or ground color with an apricot-khaki band delimited by a bright red-orange line with slight inward bleeding. The main color of the blade ages to almost white.
*Petal color* (*adaxial surface, freshly opened*).—Ground color of blade: 69C, 69D, 49D and 36D are all present. Color of band (considered to overlay the blade): 42D to 43B. Color of line delimiting color of blade and band: 42A.
*Petal color* (*adaxial surface, fully open and mature*).—Ground color of blade: N155B. Color of band (considered to overlay the blade): 23D, 24D and 25D are all present. Color of line delimiting color of blade and band: 42D to 43D. Color of middle of strap: 145C. Color of base of strap: 145D.
*Petal color* (*abaxial surface*).—Ground color of blade freshly opened: 69A. Ground color of blade, fully open and mature: 69C. Overlaying band: Absent on abaxial surface. Color of middle of strap: 145C. Color of base of strap: 145D.

Calyx:
*Dimensions*.—30 mm in length and 9 mm in width.
*Shape*.—Cylindrical.
*Sepals*.—5, fused to 7 mm below the apex.
*Sepal dimensions*.—31 mm in length and 7 mm in width.
*Apex*.—Acute.
*Base*.—Truncate.
*Color of sepals, outer surface*.—137B fading to 137D at base.
*Color of sepals, inner surface*.—139C to 139D.
*Anthocyanin*.—Absent.
*Splitting*.—Not observed.

Epicalyx:
*Arrangement*.—Two pairs of bracts, of which one pair (inner epicalyx or bracteoles) is closest to the calyx, and one pair forms an outer epicalyx.
*Bracts shape*.—Medium acuminate.
*Bracts position*.—Both pairs adpressed to each other and to the calyx, and free.
*Bracts dimensions* (*outer epicalyx*).—12 mm in length and 6 mm in width.
*Bracts dimensions* (*inner epicalyx*).—11 mm in length and 11 mm in width.
*Bracts color*.—N138C, N138D and 138D are all present.
*Anthocyanin*.—Absent.

Reproductive organs:
*Stamen number*.—10 stamens.
*Stamen dimensions*.—30 mm length and 0.5 mm diameter.
*Color of filaments*.—NN155D.
*Anther number*.—10.
*Anther dimensions*.—4 mm length and 1 mm in diameter.
*Color of anthers*.—NN155D.
*Anther attachment*.—Dorsifixed.
*Pollen*.—Present, dust color close to 156D.
*Style number*.—2.
*Style shoulder*.—Absent.
*Color of style*.—NN155D.
*Style dimensions*.—30 mm to 35 mm in length and 1 mm in width.
*Stigma number*.—One on each style.
*Stigma shape*.—Linear, along the top of the style when mature, with a bilobed extremity.
*Stigma color*.—Pink hue.
*Stigma dimensions*.—Approximately 6 mm in length, along the style.
*Ovary position*.—Superior.
*Ovary dimensions*.—11 mm in length and 5 mm in diameter.
*Ovary shape*.—Obovate.
*Ovary surface and texture*.—Smooth and slightly ribbed.
*Ovary color*.—144C and 145A at the uppermost surface, becoming paler 145C to 145D at the lowest surface.

Seed:
*Color*.—202A.
*Length*.—3 mm.
*Diameter*.—2 mm.
*Shape*.—Oval and flattened.
*Surface*.—Crinkled.
*Number*.—Varies, up to 20 per pod.

Diseases and pests: Susceptible to known *Dianthus* pests and disease but no other susceptibilities to pests or disease are known.

COMPARISON WITH PARENTAL LINE AND KNOWN VARIETY

The comparison with the parents is not possible as 'WP15 PIE45' was selected from the open pollination of a group of unnamed and unreleased seedlings of *Dianthus* in the group *Dianthus* x *allwoodii* hort., all characterized by large single flowers.

The variety of *Dianthus* considered to most closely resemble 'WP15 PIE45' is the inventor's variety *Dianthus* Plant Named 'WP15 PIE41' (co-pending U.S. application Ser. No. 15/731,062). In comparison with 'WP15 PIE45', 'WP15 PIE41' has slightly shorter flower stems and bears white single flowers with a lime-colored eye.

I claim:

1. A new and distinct cultivar of *Dianthus* plant named 'WP15 PIE45' as described and illustrated herein.

* * * * *